(12) United States Patent
Emilsson et al.

(10) Patent No.: US 11,236,216 B2
(45) Date of Patent: Feb. 1, 2022

(54) MANUFACTURING PROCESS FOR POLYSACCHARIDE BEADS

(71) Applicant: Cytiva BioProcess R&D AB, Uppsala (SE)

(72) Inventors: Per Erik Emilsson, Uppsala (SE); Susanna Klara Margareta Lindberg, Uppsala (SE); Jonny Wernersson, Uppsala (SE); Jonas Gustafsson, Uppsala (SE); Adam Hurynowicz, Uppsala (SE)

(73) Assignee: Cytiva BioProcess R & D AB, Uppsala (SE)

( * ) Notice: Subject to any disclaimer, the term of this patent is extended or adjusted under 35 U.S.C. 154(b) by 277 days.

(21) Appl. No.: 15/578,074

(22) PCT Filed: May 27, 2016

(86) PCT No.: PCT/EP2016/062050
§ 371 (c)(1),
(2) Date: Nov. 29, 2017

(87) PCT Pub. No.: WO2016/193163
PCT Pub. Date: Dec. 8, 2016

(65) Prior Publication Data
US 2018/0291184 A1  Oct. 11, 2018

(30) Foreign Application Priority Data
Jun. 4, 2015 (GB) .................... 1509677

(51) Int. Cl.
| C08L 5/02 | (2006.01) |
| C08B 37/02 | (2006.01) |
| B01J 13/14 | (2006.01) |
| C07K 1/22 | (2006.01) |
| C12N 5/00 | (2006.01) |

(52) U.S. Cl.
CPC ............... *C08L 5/02* (2013.01); *B01J 13/14* (2013.01); *C07K 1/22* (2013.01); *C08B 37/0021* (2013.01); *C12N 5/0075* (2013.01); *C08L 2203/02* (2013.01); *C08L 2205/02* (2013.01); *C12N 2531/00* (2013.01); *C12N 2533/70* (2013.01); *C12N 2533/78* (2013.01); *C12N 2537/10* (2013.01)

(58) Field of Classification Search
None
See application file for complete search history.

(56) References Cited

U.S. PATENT DOCUMENTS

| 2,828,180 | A | * | 3/1958 | Sertorio | ............. | C09B 67/0071 |
| | | | | | | 8/607 |
| 4,710,454 | A | * | 12/1987 | Langen | ............. | G03C 7/396 |
| | | | | | | 430/546 |
| 4,863,972 | A | * | 9/1989 | Itagaki | ............. | B01D 15/34 |
| | | | | | | 521/141 |
| 5,935,941 | A | * | 8/1999 | Pitha | ............. | C08B 37/0015 |
| | | | | | | 514/58 |
| 2003/0069319 | A1 | * | 4/2003 | Fujimaru | ............. | C08F 2/32 |
| | | | | | | 521/50 |
| 2013/0202810 | A1 | * | 8/2013 | Nakano | ............. | H02N 1/00 |
| | | | | | | 427/532 |

FOREIGN PATENT DOCUMENTS

| CN | 1078724 A | 11/1993 |
| EP | 0188084 A2 | 7/1986 |
| GB | 974054 | 11/1964 |
| GB | 1244990 | 9/1971 |
| WO | 91/01721 A1 | 2/1991 |
| WO | 97/38018 A1 | 10/1997 |
| WO | 2012/028623 A1 | 3/2012 |

OTHER PUBLICATIONS

Wiedenhof et al. Die Starke (1969) 21(5): 119-123 (Year: 1969).*
Constantin et al. Int. J. Pharmaceutics (2007) 330: 129-137 (Year: 2007).*
Product Data Sheet for cellulose acetate butyrate published by Eastman Co. (2006) (Year: 2006).*
Product Data Sheet for Nonident P40 from VWR Life Sciences downloaded from https://us.vwr.com/store/product/7422690/nonidet-p-40-substitute-np-40-reagent-grade on Jan. 16, 2020. (Year: 2020).*
Definition of "emulsion" from https://medical-dictionary.thefreedictionary.com/emulsion downloaded Jan. 17, 2020 (Year: 2020).*
Kenari et al. Applied Polymer Sci. (2013 (online May 22, 2012) DOI: 10.1002/APP.37983, Wileyonlinelibrary.com/app, pp. 3712-3724 (Year: 2013).*
PCT International Search Report and Written Opinion for PCT Application No. PCT/EP2016/062050 dated Aug. 8, 2016 (9 pages).
GB Search Report for GB Application No. 1509677.9 dated Nov. 18, 2015 (5 pages).
Chengdu Branch of Chenguang, 1993, XP002760227, abstract for CN 19931010973; downloaded from WPI/Thompson.
Bandrup et al., "Solubility Parameter Values," Polymer Handbook, 1989, VII/540-VII-544.
Hagel, "GEL Filtration: Size Exclusion Chromatography," Protein Purification, 2011, pp. 51-91.

\* cited by examiner

*Primary Examiner* — Susan M Hanley (74) *Attorney, Agent, or Firm* — Eversheds Sutherland (US) LLP (57) ABSTRACT

The invention discloses a method of manufacturing polysaccharide beads, comprising the steps of: i) providing a water phase comprising an aqueous solution of a polysaccharide; ii) providing an oil phase comprising at least one water-immiscible organic solvent and at least one oil-soluble emulsifier; iii) emulsifying the water phase in the oil phase to form a water-in-oil (w/o) emulsion; and iv) inducing solidification of the water phase in the w/o emulsion, wherein the organic solvent is an aliphatic or alicyclic ketone or ether.

21 Claims, 7 Drawing Sheets

MANUFACTURING PROCESS FOR POLYSACCHARIDE BEADS

CROSS REFERENCE TO RELATED APPLICATIONS

This application claims the priority benefit of PCT/EP2016/062050 filed on May 27, 2016 which claims priority benefit of Great Britain Application No. 1509677.9 filed June 4, 2015. The entire contents of which are hereby incorporated by reference herein.

TECHNICAL FIELD OF THE INVENTION

The present invention relates to polysaccharide beads, and more particularly to manufacture of polysaccharide beads by inverse suspension techniques. The invention also relates to crosslinked polysaccharide beads and to use of the beads for separation purposes.

BACKGROUND OF THE INVENTION

Crosslinked polysaccharide beads are commonly used as stationary phases for chromatographic separation of proteins and other biomolecules. Such beads were introduced in the early 1960-ies (see e.g. U.S. Pat. No. 3,208,994, which is hereby incorporated by reference in its entirety), mainly for laboratory separation purposes. Since then their use has grown dramatically and crosslinked polysaccharide beads are now used routinely in large scale manufacturing processes for separation of many biopharmaceuticals such as monoclonal antibodies, plasma components, insulin and various recombinant proteins.

The most common way to prepare polysaccharide beads is by inverse suspension processes, where an aqueous solution of a polysaccharide is emulsified as a water-in-oil (w/o) emulsion in a continuous oil phase and the emulsion droplets are solidified either by crosslinking or by thermal gelation. Such processes are described in e.g. U.S. Pat. Nos. 3,208,994, 4,794,177 and 6,602,990 (hereby incorporated by reference in their entireties), which use chlorinated hydrocarbons or aromatic hydrocarbons as the oil phase. An issue here is that large scale use of halogenated hydrocarbons and aromatic hydrocarbons is currently being phased out for environmental reasons.

Accordingly there is a need for methods to manufacture polysaccharide beads without the use of halogenated or aromatic solvents.

SUMMARY OF THE INVENTION

One aspect of the invention is to provide an environmentally acceptable method of manufacturing polysaccharide beads. This is achieved with a method as defined in the claims.

One advantage is that the method does not use halogenated or aromatic solvents. Further advantages are that spherical beads with good pore structures and mechanical properties can be obtained.

A second aspect of the invention is to provide a polysaccharide bead suitable for separation purposes. This is achieved with a bead as defined in the claims.

A third aspect of the invention is to provide a use for separation purposes of the crosslinked beads. This is achieved with a use as defined in the claims.

Further suitable embodiments of the invention are described in the dependent claims.

DETAILED DESCRIPTION OF EMBODIMENTS

Figure 1:
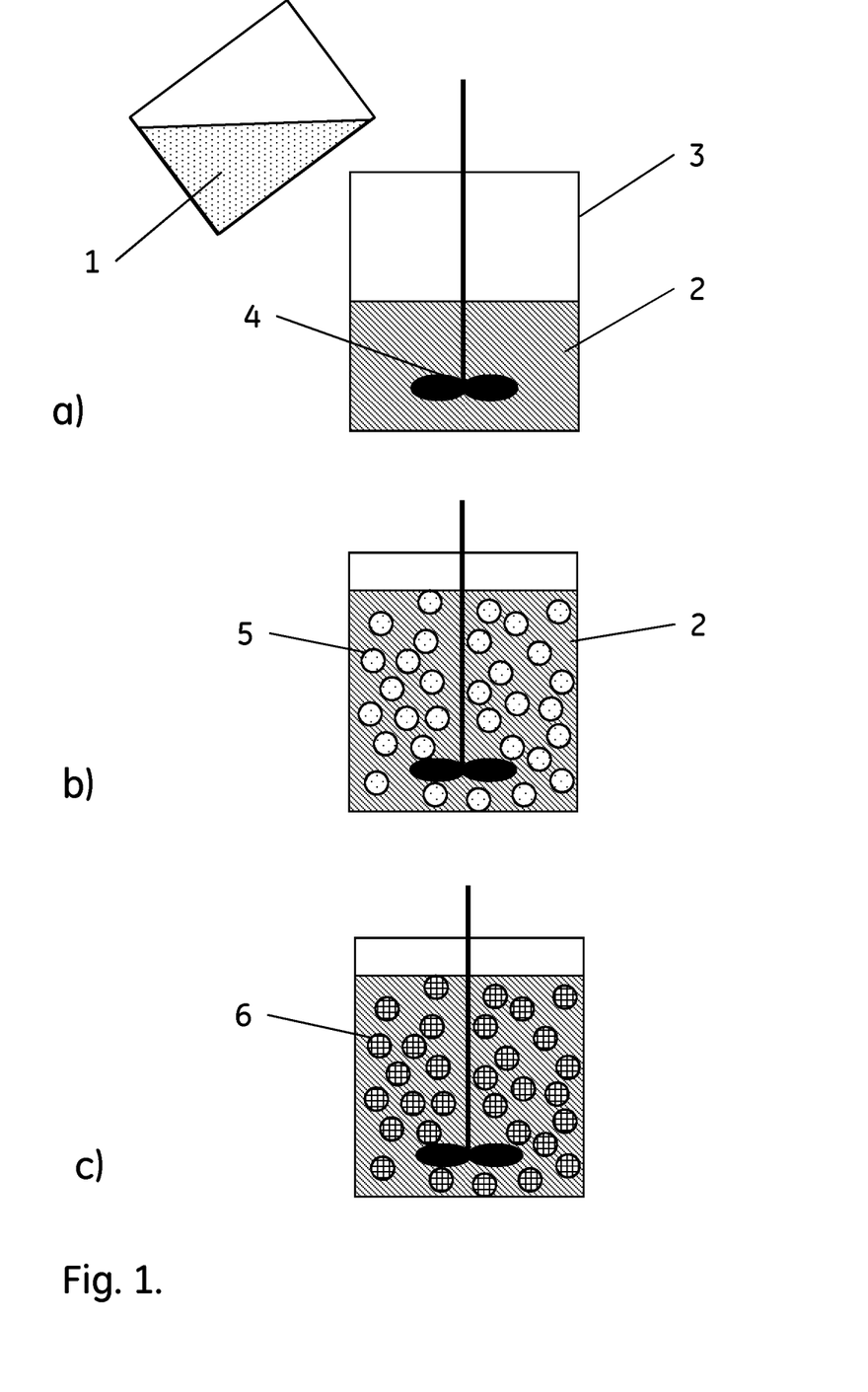
FIG. 1 shows an outline of the method of the invention. a) addition of the water phase to the oil phase, b) water-in-oil emulsion, c) solidified beads dispersed in oil phase.
Figure 2:
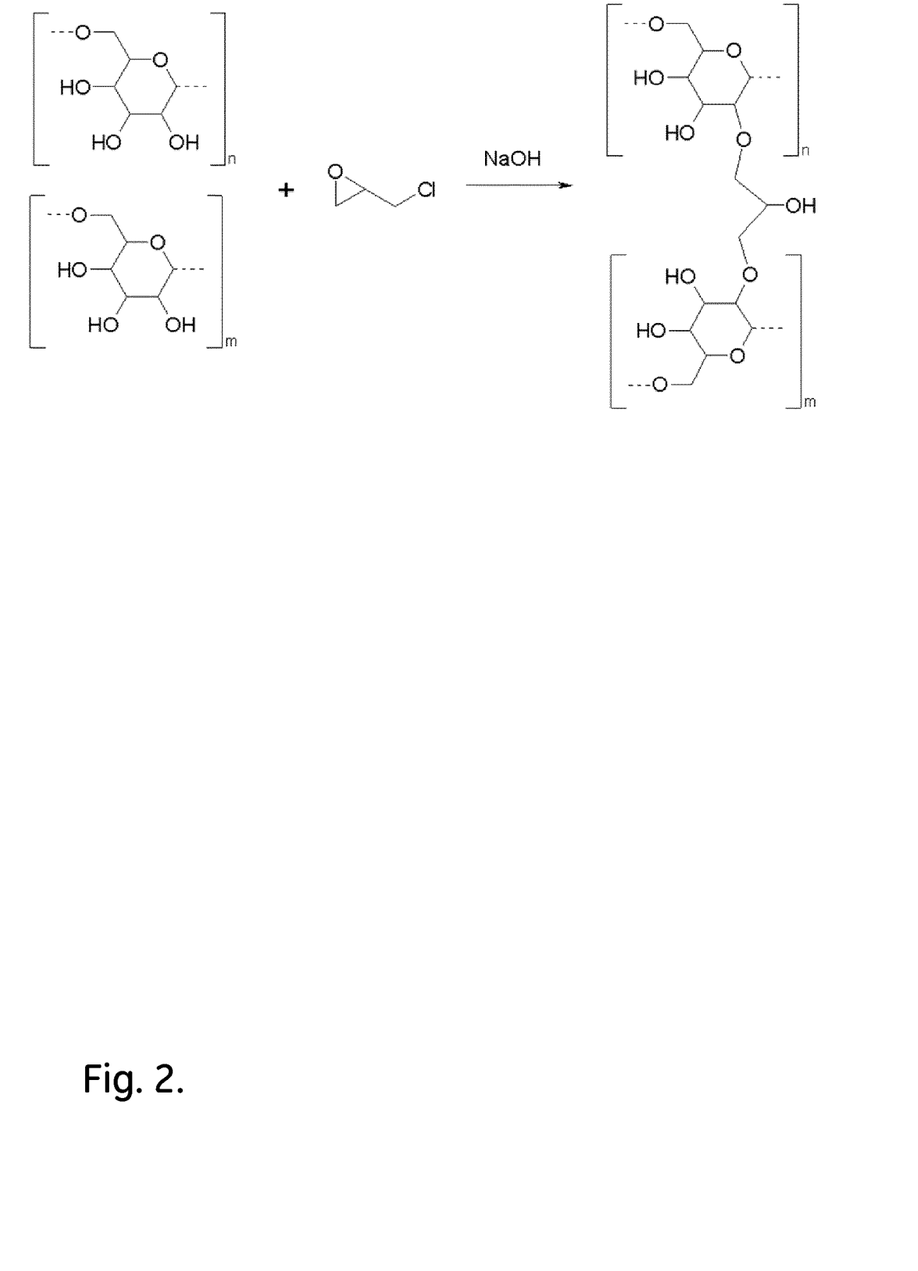
FIG. 2 shows the crosslinking of dextran with epichlorohydrin according to an embodiment of the invention.
Figure 3:
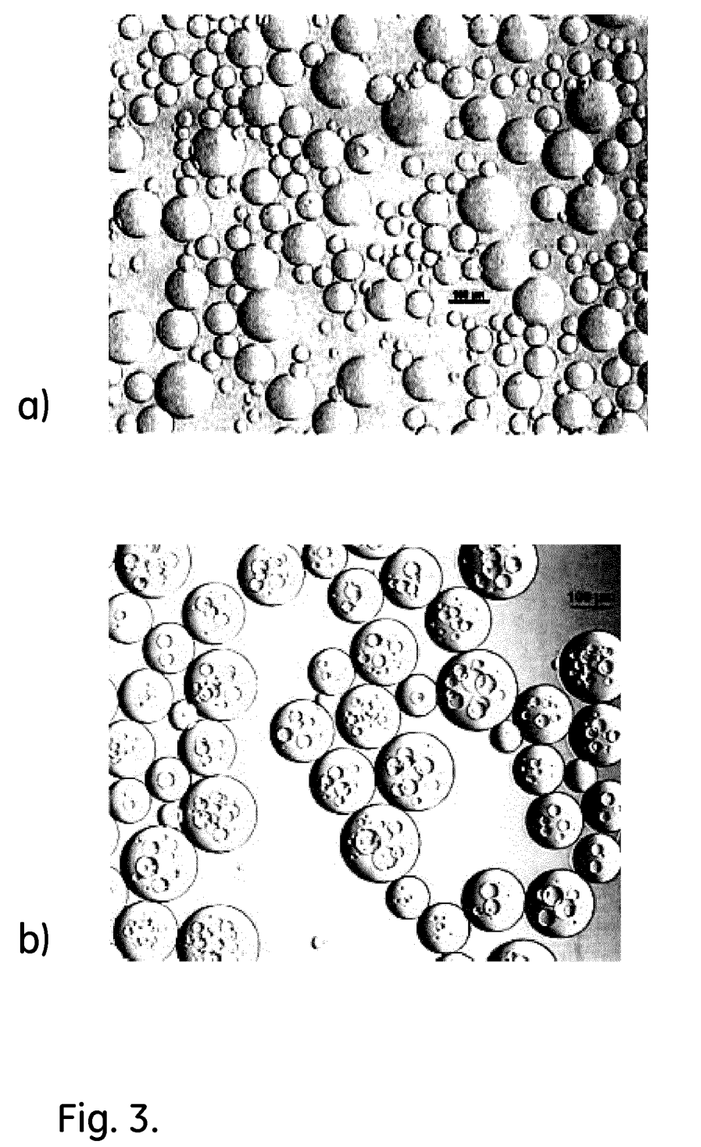
FIG. 3 shows microscope pictures of the swollen particles from a) sample 9090 (2-MCH) and b) sample 5595 (3-MCH).
Figure 4:
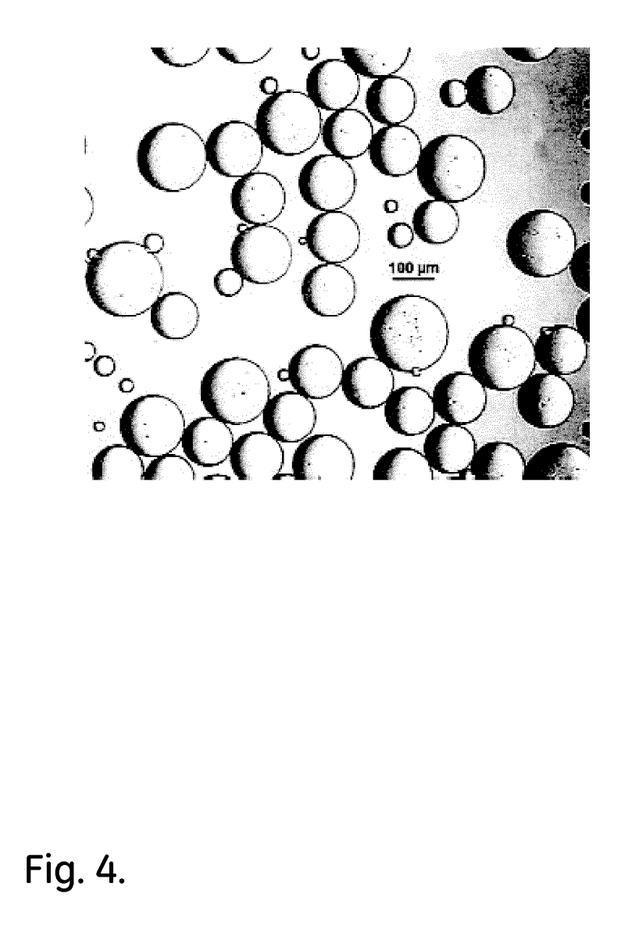
FIG. 4 shows microscope pictures of the swollen particles from sample 5624 (cyclohexane+3-MCH).
Figure 5:
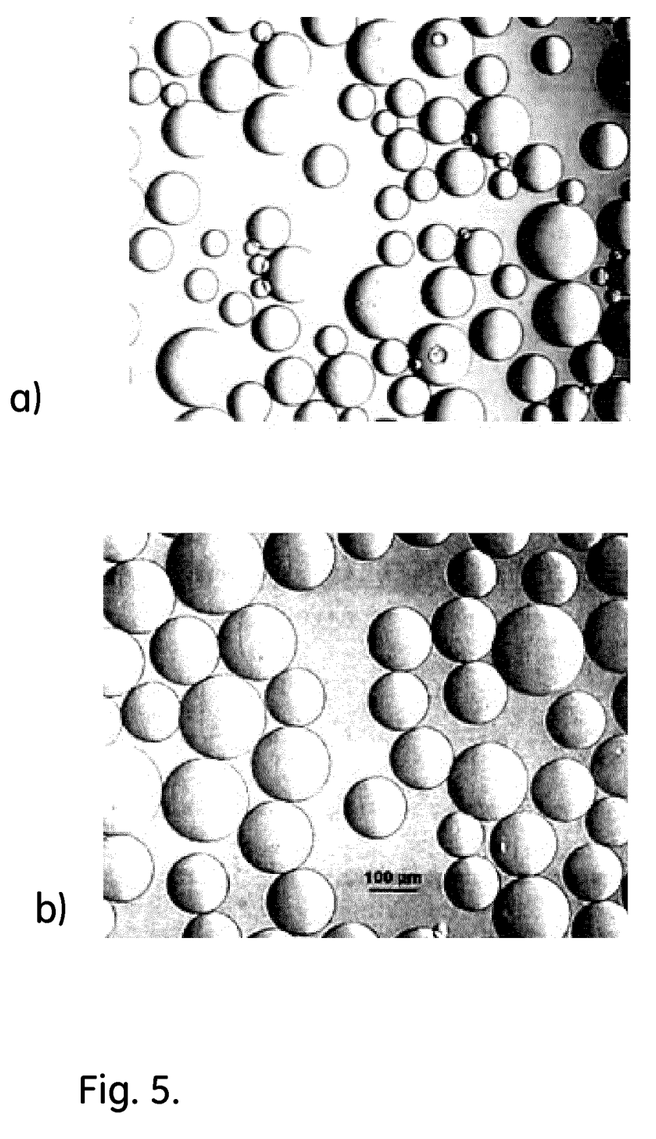
FIG. 5 shows microscope pictures of the swollen particles from a) sample 6462 (CPME) and b) sample 5182 (CPME+3-MCH).
Figure 6:
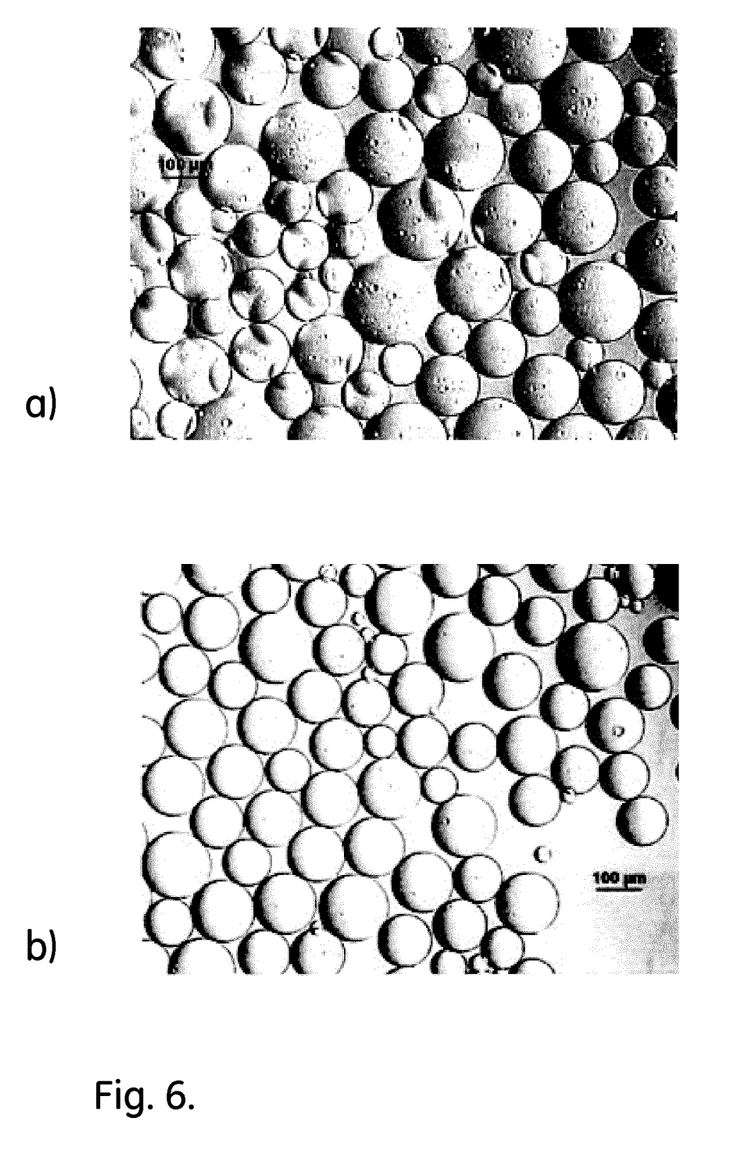
FIG. 6 shows microscope pictures of the swollen particles from a) sample 6671 (DIBK) and b) sample 5382 (DIBK+3-MCH).
Figure 7:
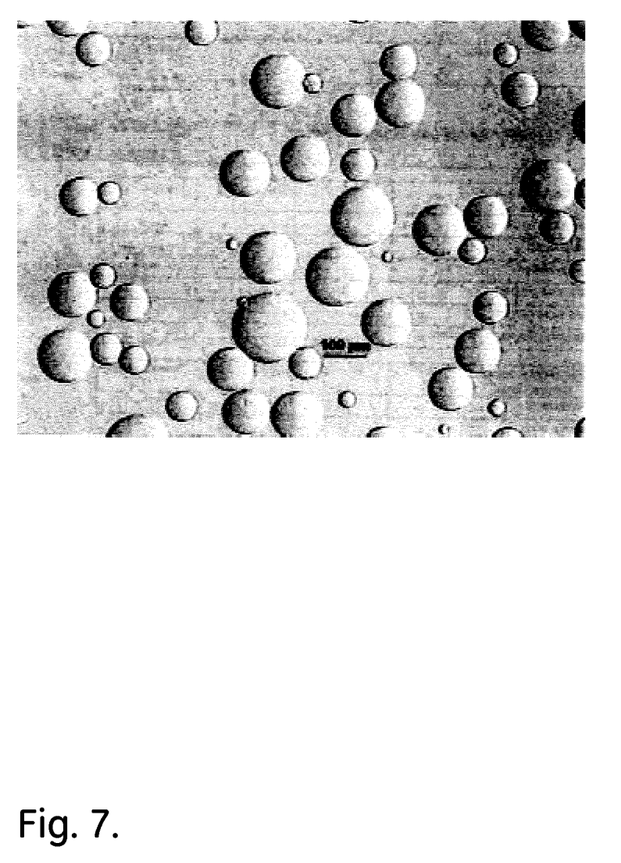
FIG. 7 shows microscope pictures of the swollen particles from sample 9355 (MAK).

In one aspect, illustrated by FIGS. 1-2, the present invention discloses a method of manufacturing polysaccharide beads, comprising the steps of:

i) Providing a water phase 1 comprising an aqueous solution of a polysaccharide. This can be accomplished by dissolving a polysaccharide in water or in water comprising one or more additional components such as salts, buffers, alkali, reducing agents etc. The polysaccharide can e.g. be a native polysaccharide such as dextran, pullulan, starch, alginate, guar gum, locust bean gum, konjac, agar, agarose, carrageenan etc. As an example, the polysaccharide can be dextran, e.g. dextran with a weight average molecular weight, Mw, of 20-4000 kDa, 40-2000 kDa or 100-500 kDa. Alternatively, the polysaccharide can be a derivative of a native polysaccharide, such as a cellulose ether, an agarose ether, a starch ether, DEAE dextran etc. Advantageously, the polysaccharide is water-soluble at room temperature or at elevated temperatures.

ii) Providing an oil phase 2 comprising at least one water-immiscible organic solvent and at least one oil-soluble emulsifier. The water-immiscible organic solvent(s) can suitably have a water solubility of less than 5 vol. %, such as less than 3 vol. % or less than 2 vol. % at 25° C. and the solubility of water in the water-immiscible organic solvent(s) can suitably be less than 5 vol. %, such as less than 3 vol. % or less than 2 vol. % at 25° C. The oil-soluble emulsifier(s) can suitably be soluble in the organic solvent(s) and the oil phase can be prepared by dissolving one or more oil-soluble emulsifiers in the water-immiscible organic solvent or a mixture of water-immiscible organic solvents. The concentration of the emulsifier in the oil phase can e.g. be 0.01-0.5 g/ml, such as 0.05-0.3 g/ml. These values can also refer to the total concentration of emulsifiers in the oil phase, in case mixed emulsifiers are used. If a polymeric emulsifier is used, the viscosity of the oil phase may vary with the molecular weight and concentration of the emulsifier.

iii) Emulsifying the water phase in the oil phase to form a water-in-oil (w/o) emulsion. As illustrated in FIG. 1, this can e.g. be done by adding the water phase 1 to the oil phase 2 in an emulsification vessel 3 under agitation provided by an agitator 4, such that the water phase is dispersed as discrete liquid droplets 5 in the continuous oil phase 2, stabilized by the emulsifier. Other techniques known in the art can also be used, e.g. continuous emulsification using static mixers, membrane emulsification etc. Depending on the viscosity of the oil phase, some optimization of the agitation intensity may be required to achieve specific particle sizes of the beads produced. Alternatively (or additionally), the concentration and/or type of the emulsifier may be varied in order to get certain particle sizes.

iv) Inducing solidification of the water phase in the w/o emulsion. This means that the liquid droplets 5 are converted to (solid) gel beads 6 by gelation of the polysaccharide. The gelation can be induced e.g. by adding a crosslinking agent to chemically (covalently) crosslink the polysaccharide, as further discussed below, or by lowering the temperature to cause thermal gelation of the polysaccharide, as is also discussed below. Once the water phase droplets have been solidified into gel beads, the beads may be recovered by sedimentation and/or filtration and they may be further washed and processed to provide beads suitable for separation or cell cultivation purposes. The further processing may e.g. include further crosslinking steps and/or derivatisation with reagents to introduce functional groups.

The at least one organic solvent is an aliphatic or alicyclic ketone or ether. Alternatively, or additionally, the at least one organic solvent does not contain halogens (i.e. the molecules of the solvent do not contain halogen atoms) and has Hansen solubility parameter values in the ranges of $\delta D=15.0\text{-}18.5$ $MPa^{1/2}$, $\delta P=3.5\text{-}8.5$ $MPa^{1/2}$ and $\delta H=4.0\text{-}5.5$ $MPa^{1/2}$. The oil phase can also comprise a mixture of halogen-free water-immiscible organic solvents, where the mixture has Hansen solubility parameter values in the ranges of $\delta D=15.0\text{-}18.5$ $MPa^{1/2}$, $\delta P=3.5\text{-}8.5$ $MPa^{1/2}$ and $\delta H=4.0\text{-}5.5$ $MPa^{1/2}$. Suitably, the content of halogenated solvents in the oil phase can be less than 1 mol %, such as less than 0.1% or less than 0.01%. The Hansen solubility parameters are discussed in detail in C M Hansen: The three dimensional solubility parameter and solvent diffusion coefficient—Their importance in surface coating formulation, Copenhagen 1967. $\delta D$ is the dispersion force contribution to the solubility parameter (cohesive energy density) of a solvent, while $\delta P$ is the polar force contribution and $\delta H$ is the hydrogen bonding force contribution. Tables of Hansen solubility parameters for different solvents can be found e.g. in J Brandrup, E H Immergut Eds. Polymer Handbook, $3^{rd}$ edition, John Wiley & Sons 1989, pp. VII/540-VII/544.

In certain embodiments, illustrated by FIG. 2, step iv) comprises crosslinking the polysaccharide. This can be accomplished e.g. by adding a crosslinking agent to the w/o emulsion. The crosslinking agent may e.g. be a compound with two electrophilic functionalities, which can react e.g. with two hydroxyl groups on the polysaccharide and cause crosslinking by the formation of covalently bonded links between polysaccharide chains. The hydroxyl groups are particularly nucleophilic at high pH conditions and it can be advantageous to use a high pH water phase in the method, e.g. by adding NaOH or other suitable alkali (e.g. KOH) to the water phase. The alkali (NaOH or KOH) concentration in the water phase may e.g. be at least 0.1 M, such as 0.1-2 M or 0.5-1 M. Examples of electrophilic crosslinkers include epichlorohydrin, diepoxides and multifunctional epoxides, as well as divinylsulfone and halohydrins like 1,3-dibromo-propanol-2. The crosslinker can suitably be added to the w/o emulsion, such that it dissolves in the oil phase and diffuses into the water phase droplets.

In some embodiments, step iv) comprises thermal gelation of the polysaccharide. In this case, the polysaccharide can be a hot-water soluble polysaccharide that forms a gel upon cooling. Examples of such polysaccharides are e.g. agar and agarose, which are soluble at temperatures of about 60° C. and higher but form solid gels upon cooling to e.g. about 40° C. or lower. In this case, steps i)-iii) can be performed at a temperature where the polysaccharide is soluble and in step iv) the temperature is lowered to a temperature below the gel point of the particular polysaccharide used.

In certain embodiments, at least one emulsifier is a cellulose derivative, such as a cellulose ester or a cellulose ether. Among cellulose esters, cellulose mixed esters, such as cellulose acetate butyrate can be particularly useful. Cellulose acetate butyrate (CAB) of different grades is commercially available, e.g. from Eastman Chemical Company (USA). The molecular weight of the CAB can suitably be 10-100 kDa, such as 15-75 kDa or 16-70 kDa, determined by gel permeation chromatography as the polystyrene equivalent number average molecular weight (Mn). The acetyl and butyryl contents can e.g. be 2-20 wt. % acetyl content and 20-60 wt. % butyryl content, such as a) 10-15 wt. % acetyl content and 30-40 wt. % butyryl content or b) 2-5 wt. % acetyl content and 50-60 wt. % butyryl content or c) 2-15 wt. % acetyl content and 30-60 wt. % butyryl content. An example of a cellulose ether useful as an emulsifier is ethyl cellulose.

In some embodiments at least one organic solvent is a $C_6$-$C_{10}$ aliphatic or alicyclic ketone or ether, such as a $C_6$-$C_{10}$ alicyclic ketone or ether. Examples of such solvents are those defined by Formula I, II or III, wherein:
$R_1$ and $R_2$ are, independently of each other, $C_1$-$C_5$ alkyl groups;
$R_3$ is a $C_1$-$C_5$ alkylene group;
$R_4$ is hydrogen or a $C_1$-$C_5$ alkyl group attached to any one of the non-carbonyl carbon atoms in the ring structure; and
$R_5$ and $R_6$ are, independently of each other, $C_1$-$C_6$ alkyl or cycloalkyl groups.

In some embodiments, at least one organic solvent is defined by Formula II, with $R_3$ and $R_4$ defined as above. $R_3$ may e.g. be a $C_2$ alkylene group and $R_4$ may be a methyl group.

In certain embodiments, the organic solvent can be selected from the group consisting of 2-methylcyclohexanone, 3-methylcyclohexanone, 4-methylcyclohexanone, cyclohexanone, diisobutyl ketone, methyl n-amyl ketone, methyl isoamyl ketone, methyl isobutyl ketone, cyclopentyl methyl ether and their mixtures. At least one organic solvent can e.g. be selected from the group consisting of 2-methylcyclohexanone, 3-methylcyclohexanone, 4-methylcyclohexanone, cyclohexanone, methyl n-amyl ketone, methyl isoamyl ketone, methyl isobutyl ketone and cyclopentyl methyl ether, such as from the group consisting of 2-methylcyclohexanone, 3-methylcyclohexanone, 4-methylcyclohexanone and cyclohexanone. In specific cases at least one organic solvent can be 2-methylcyclohexanone.

In a second aspect the invention discloses a polysaccharide bead, or a plurality of polysaccharide beads, prepared by the method of any embodiment disclosed above. The invention also discloses a crosslinked polysaccharide bead, or a plurality of crosslinked polysaccharide beads, comprising at least 0.1 ppm, such as 0.1-100 ppm of a $C_6$-$C_{10}$ aliphatic or alicyclic ketone or ether. This may e.g. constitute solvent residues from a manufacturing process as discussed above. The amount may be measured e.g. by headspace GC or GC analysis of extracts, using e.g. mass spectroscopy or flame ionization as detection method. The $C_6$-$C_{10}$ aliphatic or alicyclic ketone or ether can be as defined by Formulas I, II or III as discussed above and it can e.g. be selected from the group consisting of 2-methylcyclohexanone, 3-methylcyclohexanone, 4-methylcyclohexanone, cyclohexanone, diisobutylketone, methyl n-amylketone, methyl isoamyl ketone, methyl isobutyl ketone, cyclopentyl methyl ether and their mixtures.

In some embodiments, the bead or plurality of beads have a diameter of 40-125 µm in dry form. In the case of a plurality of beads, the diameter can be determined as the volume-weighted median diameter, d50v, e.g. by laser light diffraction or by electrozone sensing counting techniques.

In certain embodiments, the bead or plurality of beads comprise at least 0.1 mmol/g, or 1-6 mmol/g, covalently bonded charged groups, such as carboxymethyl-, sulfopropyl-, diethyl aminoethyl-, and/or diethyl-(2-hydroxy-propyl) aminoethyl-groups. Such groups are useful for ion exchange separations and groups like diethyl aminoethyl groups can also promote the growth of adherent cells when the beads are used as microcarriers in cell cultivation. The derivatisation with charged groups can be accomplished by methods well known in the art.

In a third aspect, the invention discloses the use of one or more polysaccharide beads as described above for separation of a target biomolecule, such as a target protein, from impurities or contaminants.

In a fourth aspect, the invention discloses the use of one or more polysaccharide beads as described above as microcarriers for cultivation of cells.

Examples

Emulsification method (reference example with 1,2-dichloroethane) 165 g dextran of Mw 150-250 kD was dissolved in 390 ml distilled water and simultaneously 22 ml 50% sodium hydroxide (NaOH) was added under stirring. 0.8 g sodium borohydride ($NaBH_4$) was added to the solution.

21 g cellulose acetate butyrate (CAB) was added into a 1000 ml glass reactor with an overhead agitator. The agitator was started and 350 ml 1,2-dichloroethane (EDC) was added (the CAB concentration was thus 0.060 g/ml EDC). The solution was stirred until the CAB had dissolved. The water phase was then added to the oil phase under agitation at 50° C. and the agitation was continued until a suitable droplet size had been reached, as judged from microscopy of small samples withdrawn. When a suitable size was obtained, the emulsion was immediately stabilised by adding 22.4 ml epichlorohydrin (ECH) to crosslink the dextran and thus solidifying the droplets. 20 minutes after the addition of ECH, 50 ml of EDC was added to make the reaction mixture less viscous and easier to agitate.

The crosslinking reaction was terminated after 20±4 h by adding 500 ml acetone. The reaction mixture was then transferred to a 3000 ml glass reactor containing 1250 ml acetone. The solution was stirred for 30 min and then the gel was subsequently allowed to sediment. The supernatant was decanted and the washing procedure was repeated 5 times with acetone and then 7 times with 60% aqueous ethanol and 4 times with 95% ethanol. The gel was then dried under vacuum at 60° C. for 48 h and the resulting powder was sieved between 40 and 100 µm sieves.

The results from five repetitions of this experiment are shown in Table 2, as samples 3077, 3088, 3092, 3081 and 1175.

SEC Analysis

Approximately 3-4 grams of powder was weighed in a plastic bottle to which roughly 100 ml of either a 9 mg/ml NaCl solution or the running buffer (0.15M NaCl+0.05 M phosphate buffer, pH 7.0) was added. The gel was left to swell and sediment for at least 16 hours. It was then washed several times and diluted in the running buffer to generate a 50-60% gel slurry. Columns of 10 mm diameter and 30 cm height (GE Healthcare HR10/30) were packed with the initial flow rate of either 1.0 or 1.2 ml/min, and the final flow rate was either 1.2 or 1.7 ml/min. The packed columns were then tested in an effectiveness test and evaluated through selectivity tests with dextran standards and proteins as described in L Hagel: pp. 51-87 in J C Janson (Ed): Protein Purification: Principles, High Resolution Methods, and Applications, $3^{rd}$ edition, Wiley 2011. The test proteins were alpha chymotrypsinogen type II, bovine (Mw 26 kDa), ribonuclease A, bovine (Mw 13.7 kDa) and lysozyme, chicken (Mw 14.3 kDa), with 0.15 M NaCl, 0.05M Sodium Phosphate, pH 7.0 as running buffer. $K_D$ data (i.e. the fraction of the bead volume accessible for a probe molecule of a particular size) for these proteins on the prototypes are shown in Table 3.

Water Regain

Water regain (Wr) is the amount of water taken up inside the beads for 1 g dry beads. A high Wr value indicates that the swollen gel is less dense and can separate high Mw target molecules. 15 g of dry beads were equilibrated with 500 ml water for 24 h. A 3.3×11.5 cm weighed centrifuge tube with a 10 µm bottom filter was filled with the gel slurry and centrifuged at 1800 rpm for 10 min. After determining the wet weight of the tube, it was dried over night at 105° C. and the dry weight was determined. The water regain was calculated as the drying weight loss (as ml water) per g dry gel.

Particle Size Distribution

The particle size distribution was measured in a Coulter Multisizer (Beckman Coulter), using the electrozone sensing technique.

Microscopic Examination

After crosslinking, the beads were examined in a light microscope with phase contrast optics and the presence of surface dimples, inclusions, aggregates etc. was noted.

Emulsifications with Different Solvents
Solvent Abbreviations
CPME—Cyclopentyl methyl ether
DIBK—Diisobutyl ketone (2,6-dimethyl-4-heptanone)
EDC—1,2-dichloroethane
MAK—Methyl n-amyl ketone
2-MCH—2-methylcyclohexanone
3-MCH—3-methylcyclohexanone
4-MCH—4-methylcyclohexanone Emulsifications were carried out according to the reference example above, with other solvents replacing EDC, and in some cases with different types and/or concentrations of CAB. The CAB types used are specified in Table 1. The beads were characterized as described above and the results are collated in Tables 2 and 3 and in the discussion below.

TABLE 1

CAB types used (all from Eastman Chemical Company and with data according to the supplier's data sheets)

| CAB type | Molecular weight*, kDa | Viscosity**, poise | Butyryl content, wt % | Acetyl content, wt % |
|---|---|---|---|---|
| 381-0.5 | 30 | 1.9 | 37 | 13 |
| 381-20 | 70 | 76 | 37 | 13.5 |
| 500-5 | 57 | 19 | 51 | 4 |
| 551-0.01 | 16 | 0.038 | 53 | 2 |

*Polystyrene equivalent number average molecular weight (Mn), as determined by gel permeation chromatography

**Viscosity determined by ASTM Method D 1343. Results converted to poises (ASTM Method D 1343) using the solution density for Formula A as stated in ASTM Method D 817 (20% Cellulose ester, 72% acetone, 8% ethyl alcohol).

TABLE 2

Results from emulsifications with different solvents and solvent combinations

| Sample | Solvent 1 | Solvent 2 | CAB type | CAB conc. g/ml | Wr (ml/g) | d50v (μm) |
|---|---|---|---|---|---|---|
| 3077 | EDC | — | 381-20 | 0.060 | 4.93 | 70.5 |
| 3088 | EDC | — | 381-20 | 0.060 | 5.03 | 67.8 |
| 3092 | EDC | — | 381-20 | 0.060 | 4.96 | 70.7 |
| 3081 | EDC | — | 381-20 | 0.060 | 5.06 | 72.0 |
| 1175 | EDC | — | 381-20 | 0.060 | 4.90 | 70.9 |
| 9090 | 2-MCH | — | 381-20 | 0.060 | 4.74 | 33.1 |
| 5133 | 3-MCH | — | 381-20 | 0.060 | 4.77 | 42.4 |
| 5505 | 3-MCH | — | 381-20 | 0.054 | 4.60 | 50.7 |
| 5595 | 3-MCH | — | 381-0.5 | 0.060 | 4.94 | 72.7 |
| 5892 | 3-MCH | — | 381-0.5 | 0.090 | 5.17 | 73.6 |
| 5928 | 3-MCH | — | 500-5 | 0.060 | 5.07 | 57.0 |
| 4904 | 4-MCH | — | 381-20 | 0.060 | 4.62 | 44.5 |
| 5624 | Cyclohexane (20 vol %) | 3-MCH (80 vol %) | 381-20 | 0.060 | 4.71 | 42.3 |
| 5806 | Cyclohexane (75 vol %) | 3-MCH (25 vol %) | 551-0.01 | 0.21 | 5.15 | 68.9 |
| 6462 | CPME | — | 500-5 | 0.12 | 4.85 | 68.1 |
| 6724 | CPME | — | 551-0.01 | 0.31 | 5.93 | 66.6 |
| 5182 | CPME (75 vol %) | 3-MCH (25 vol %) | 381-20 | 0.060 | 4.83 | 68.3 |
| 5443 | CPME (75 vol %) | 3-MCH (25 vol %) | 381-20 | 0.060 | 5.07 | 52.8 |
| 5868 | CPME (75 vol %) | 3-MCH (25 vol %) | 381-20 | 0.060 | 4.97 | 70.0 |
| 6551 | DIBK | — | 500-5 | 0.080 | 4.78 | 69.2 |
| 6671 | DIBK | — | 500-5 | 0.080 | 4.94 | 71.9 |
| 6672 | DIBK | — | 551-0.01 | 0.23 | 5.50 | 61.2 |
| 5108 | DIBK (75 vol %) | 3-MCH (25 vol %) | 381-20 | 0.060 | 4.56 | 39.4 |
| 5382 | DIBK (75 vol %) | 3-MCH (25 vol %) | 381-20 | 0.060 | 4.77 | 45.0 |
| 6725 | DIBK (75 vol %) | Cyclohexanone (25 vol %) | 381-20 | 0.047 | 4.59 | 50.2 |
| 9355 | MAK | — | 381-20 | 0.060 | 4.86 | 65.8 |
| 11854 | DIBK (75 vol %) | 2-MCH (25 vol %) | 381-20 | 0.036 | 5.04 | |

TABLE 3

$K_D$ data for three test proteins in gel filtration experiments performed with prototypes packed in columns

| Sample | Alpha chymotrypsinogen | Ribonuclease | Lysozyme |
|---|---|---|---|
| 5133 | 0.077 | 0.224 | 0.409 |
| 5505 | 0.056 | 0.229 | 0.418 |
| 5595 | 0.102 | 0.281 | 0.457 |
| 5892 | 0.120 | 0.294 | 0.472 |
| 5928 | 0.105 | 0.279 | 0.468 |
| 4904 | 0.059 | 0.341 | 0.510 |
| 5624 | 0.072 | 0.213 | 0.395 |
| 5806 | 0.112 | 0.293 | 0.466 |
| 6462 | 0.106 | 0.257 | 0.435 |
| 6724 | 0.171 | 0.330 | 0.508 |
| 5182 | 0.081 | 0.248 | 0.425 |
| 5443 | 0.130 | 0.277 | 0.462 |
| 5868 | 0.115 | 0.283 | 0.461 |
| 6551 | 0.111 | 0.265 | 0.448 |
| 6671 | 0.099 | 0.257 | 0.441 |
| 6672 | 0.153 | 0.303 | 0.487 |
| 5108 | 0.017 | 0.130 | 0.337 |
| 5382 | 0.078 | 0.258 | 0.435 |
| 6725 | 0 | 0.167 | 0.403 |
| 9355 | 0.101 | 0.251 | 0.432 |
| 11854 | 0.099 | 0.259 | 0.453 |

The solvents used were also analysed by NMR spectroscopy before and after emulsification model experiments performed in the absence of dextran and the emulsifier. The spectra before and after were essentially identical, showing that no degradation occurred during the reaction conditions used. This was in contrast to an ester solvent, t-butyl acetate, which although being a sterically hindered ester, was completely hydrolysed under the strongly alkaline conditions used.

DISCUSSION

The solvents evaluated produce beads that can be used for chromatography, as evidenced e.g. by their performance in the SEC analysis. The measured properties are in the same range as for the reference prototypes, which shows that the new solvents perform well. Due to the different interactions between the solvents and the CAB emulsifier, the CAB type and concentration had to be varied in order to get suitable oil phase viscosities. The beads were generally spherical (FIGS. 7-11), but with the solvents 3-MCH and 4-MCH (particularly when used alone), some inclusions and dimples occurred on the beads.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Any patents or patent applications mentioned in the text are hereby incorporated by reference in their entireties, as if they were individually incorporated.

The invention claimed is:

1. A method of manufacturing polysaccharide beads, comprising the steps of:
   i) providing a water phase comprising an aqueous solution of a polysaccharide and an alkali, wherein the alkali is present in the water phase at a concentration of 0.1 M to 2 M;
   ii) providing an oil phase comprising at least one water-immiscible organic solvent and at least one oil-soluble emulsifier;
   iii) emulsifying said water phase in said oil phase to form a water-in-oil (w/o) emulsion; and
   iv) inducing solidification of said water phase in said w/o emulsion to form substantially spherical polysaccharide beads,
   wherein said at least one organic solvent is an alicyclic ketone or an ether.

2. A method of manufacturing polysaccharide beads, comprising the steps of:
   i) providing a water phase comprising an aqueous solution of a polysaccharide and an alkali, wherein the alkali is present in the water phase at a concentration of 0.1 M to 2 M;
   ii) providing an oil phase comprising at least one water-immiscible organic solvent and at least one oil-soluble emulsifier;
   iii) emulsifying said water phase in said oil phase to form a water-in-oil (w/o) emulsion; and
   iv) inducing solidification of said water phase in said w/o emulsion to form substantially spherical polysaccharide beads,
   wherein said at least one organic solvent is an alicyclic ketone or an ether, does not contain halogens, and has Hansen solubility parameter values in the ranges of $\delta D=15.0\text{-}18.5\ \text{MPa}^{1/2}$, $\delta P=3.5\text{-}8.5\ \text{MPa}^{1/2}$ and $\delta H=4.0\text{-}5.5\ \text{MPa}^{1/2}$, or wherein said oil phase comprises a mixture of halogen-free water-immiscible organic solvents, said mixture having Hansen solubility parameter values in the ranges of $\delta D=15.0\text{-}18.5\ \text{MPa}^{1/2}$, $\delta P=3.5\text{-}8.5\ \text{MPa}^{1/2}$ and $\delta H=4.0\text{-}5.5\ \text{MPa}^{1/2}$.

3. The method of claim 1, wherein step iv) comprises crosslinking said polysaccharide.

4. The method of claim 3, wherein in step iv) a crosslinking agent is added to said w/o emulsion.

5. The method of claim 4, wherein said crosslinking agent comprises epichlorohydrin or a diepoxide.

6. The method of claim 1, wherein said polysaccharide comprises dextran.

7. The method of claim 6, wherein said dextran has a weight average molecular weight, Mw, of 20-4000 kDa.

8. The method of claim 1, wherein the concentration of the emulsifier in the oil phase is 0.01-0.5 g/ml.

9. The method of claim 1, wherein said at least one emulsifier is a cellulose derivative.

10. The method of claim 9, wherein said at least one emulsifier is a cellulose mixed ester.

11. The method of claim 10, wherein said at least one emulsifier is cellulose acetate butyrate with an average molecular weight, Mn, of 10-100 kDa.

12. The method of claim 10, wherein said at least one emulsifier is cellulose acetate butyrate with 2-20 wt. % acetyl content and 20-60 wt. % butyryl content.

13. The method of claim 1, wherein said at least one organic solvent is a $C_6$-$C_{10}$ alicyclic ketone or ether.

14. The method of claim 1, wherein said at least one organic solvent is defined by Formula II or III, wherein:
   $R_3$ is a $C_1$-$C_5$ alkylene group;
   $R_4$ is hydrogen or a $C_1$-$C_5$ alkyl group; and
   $R_5$ and $R_6$ are, independently of each other, $C_1$-$C_6$ alkyl or cycloalkyl groups.

15. The method of claim 14, wherein said at least one organic solvent is defined by Formula II.

16. The method of claim 1, wherein said at least one organic solvent is selected from the group consisting of 2-methylcyclohexanone, 3-methylcyclohexanone, 4-methylcyclohexanone, cyclohexanone, cyclopentyl methyl ether and their mixtures.

17. The method of claim 16, wherein said at least one organic solvent is selected from the group consisting of 2-methylcyclohexanone, 3-methylcyclohexanone, 4-methylcyclohexanone and cyclohexanone.

18. The method of claim 17, wherein said at least one organic solvent is 2-methylcyclohexanone.

19. The method of claim 9, wherein said cellulose derivative is a cellulose ester.

20. The method of claim 10, wherein said cellulose mixed ester is a cellulose acetate butyrate.

21. The method of claim 11, wherein said average molecular weight, Mn, is 15l-75 kDa.

* * * * *